United States Patent [19]

Tanaka et al.

[11] Patent Number: 4,716,299
[45] Date of Patent: Dec. 29, 1987

[54] APPARATUS FOR CONVEYING AND INSPECTING A SUBSTRATE

[75] Inventors: Hiroshi Tanaka; Hiromitsu Iwata; Yukio Kakizaki, all of Yokohama, Japan

[73] Assignee: Nippon Kogaku K. K., Tokyo, Japan

[21] Appl. No.: 821,743

[22] Filed: Jan. 23, 1986

[30] Foreign Application Priority Data

Jan. 31, 1985 [JP] Japan .................................. 60-17318

[51] Int. Cl.$^4$ ............................................ G01N 21/86
[52] U.S. Cl. ...................................... 250/571; 356/445
[58] Field of Search ............... 250/571, 572, 562, 563; 356/445, 446, 447, 448

[56] References Cited

U.S. PATENT DOCUMENTS

| | | | |
|---|---|---|---|
| 4,422,547 | 12/1983 | Abe et al. | 206/328 |
| 4,468,120 | 8/1984 | Tanimoto et al. | 356/237 |
| 4,541,715 | 9/1985 | Akiyama et al. | 250/572 |
| 4,568,835 | 2/1986 | Inamura et al. | 250/572 |
| 4,598,997 | 7/1986 | Steigmeier et al. | 250/572 |
| 4,610,541 | 9/1986 | Tanimoto et al. | 250/572 |

FOREIGN PATENT DOCUMENTS

80546 11/1980 Japan .

Primary Examiner—David C. Nelms
Assistant Examiner—Jessica L. Ruoff
Attorney, Agent, or Firm—Shapiro and Shapiro

[57] ABSTRACT

An arrangement in an apparatus for handling a substrate such as a photomask or a reticle used in a process of manufacturing a semiconductor device comprises a container unit for containing therein the substrate in a substantially horizontal posture, an inspection unit having means for inspecting a surface of the substrate, the inspecting means including a radiation source for supplying a directional beam, and a device for detecting the scattering of the directional beam, a holding member for supporting the substrate substantially horizontally, a device for moving the holding member between the container unit and the inspection unit and conveying the substrate from the container unit to the inspection unit by the use of the holding member, and a scanning device for moving the holding member in a horizontal direction relative to the inspecting means and moving the substrate relative to the directional beam while subjecting the surface of the substrate to the directional beam.

11 Claims, 8 Drawing Figures

APPARATUS FOR CONVEYING AND INSPECTING A SUBSTRATE

BACKGROUND OF THE INVENTION

1. Field of the Invention

This invention relates to an apparatus for conveying a substrate such as a vitreous photomask or a reticle, and in particular to an automatic conveying apparatus suitable for incorporation into an exposure apparatus, a cleaning apparatus or the like.

2. Description of the Prior Art

In recent years, the tendency of semiconductor elements toward minuteness and high density has advanced and various performances required of apparatuses for manufacturing them, particularly, exposure apparatuses, have become severe year by year. In a reduction projection type exposure apparatus (a so-called stepper) having a high resolving power and a high superposing system, a pattern is reduction-projected onto a semiconductor wafer by the step-and-repeat system by the use of a reticle which provides the negative of pattern transfer and therefore, if a foreign particle adheres to the reticle, there is a problem that all chips on the wafer become defective. For this reason, apparatuses for conveying the reticle fully automatically without touching the reticle when the reticle is mounted onto or removed from the apparatus have been put into practical use and have achieved a great result in the field of production of semiconductor elements. Such a conveying apparatus, with an example of the reticle case mountable on the conveying apparatus, is disclosed in U.S. Pat. No. 4,422,547. In such a conventional conveying apparatus, there has been a disadvantage that various operations of delivering the reticle are complicated with the reproducibility of positioning taken into account and a long conveyance time is required. Also, in order to prevent foreign particles from adhering to the reticle, a protective frame (pellicle frame) for stretching a high molecular weight transparent pellicle spaced apart by several millimeters from the surface of the reticle has come to be adhesively secured to the reticle, and the reticle with such a pellicle could not be conveyed by the conventional apparatus. Where the transfer of a pattern is to be effected by the use of a reticle with a pellicle, it is substantially ensured that there is no foreign particle directly adhering to the surface of the reticle, but a relatively large foreign particle adhering to the surface of the pellicle greatly affects the transfer of the pattern. So, it is efficient in the manufacture of semiconductor elements to use, for a reticle without a pellicle, a strict foreign particle inspecting device capable of discriminating between the sizes of foreign particles by a resolving power of the order of 2–3 $\mu$m, and to use, for a reticle with a pellicle, a pellicle inspecting device for inspecting only a large foreign particle on the pellicle, for example, only resolvable dust of 100 $\mu$m or more. Where both of such foreign particle inspecting device and pellicle inspecting device are retrofitted to a stepper, the conveying apparatus thereof must equally convey both of a reticle with a pellicle and a reticle without a pellicle, and this has led to a problem that high-speed conveyance cannot be accomplished as long as the conventional conveying method is used.

SUMMARY OF THE INVENTION

It is an object of the present invention to overcome the above-noted disadvantages and to provide an arrangement for an apparatus in which the conveyance sequence is simplified and the period of delivery is decreased to the utmost, whereby a substrate is conveyed at a high speed.

According to the present invention, in an apparatus for conveying a substrate such as a mask or a reticle between means for containing therein the substrate horizontally and inspecting means for inspecting a foreign particle adhering to the substrate, conveying means having a holding member for holding the substrate horizontally and rectilinearly moving the holding member so as to take out the substrate horizontally from the containing means by the holding member is provided, the movement of the substrate during the foreign particle inspection by the inspecting means is accomplished by rectilinear movement of the holding member, and the single holding member provides both of a member for taking out the substrate and a substrate moving member for inspection.

DESCRIPTION OF THE PREFERRED EMBODIMENT

Figure 1:
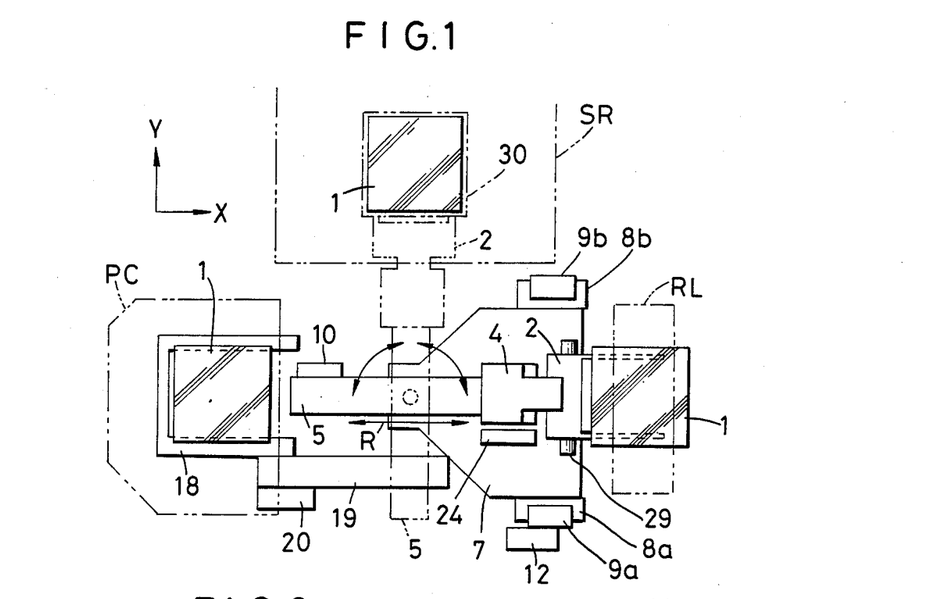
FIG. 1 is a plan view schematically showing the construction of a conveying apparatus according to an embodiment of the present invention.
Figure 2:
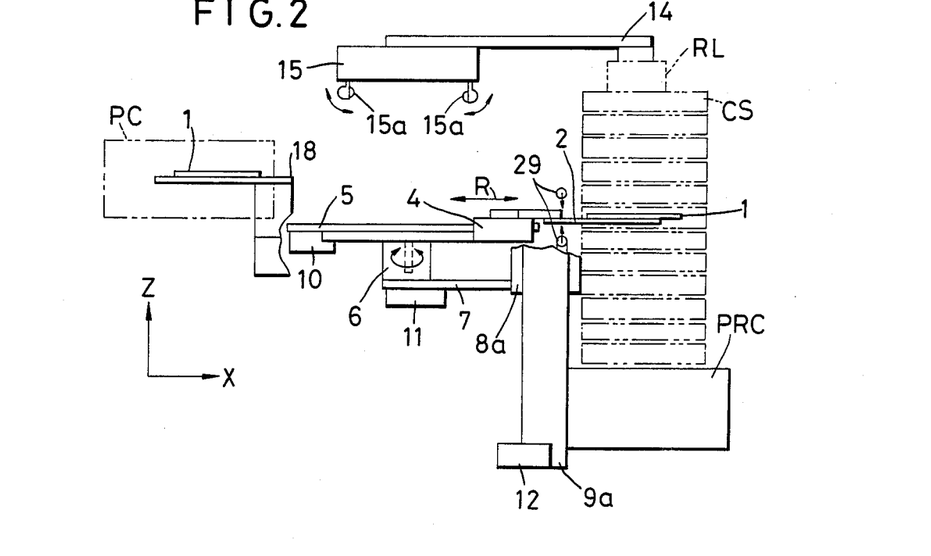
FIG. 2 is a front view of the FIG. 1 apparatus.

FIGS. 1 and 2 schematically show the construction of a conveying apparatus according to an embodiment of the present invention. A stepper SR having an illuminating light source, a projection lens system, a wafer stage, etc., not shown, with a reticle stage 30, transfers a pattern to a wafer or the like by the use of a reticle 1. The reticle 1 is designed so as to be horizontally conveyed onto the reticle stage 30 from the front of the stepper SR and placed on the stage 30. On the right-hand side short of the stepper SR as viewed from the front thereof, there is disposed a reticle library RL.

A plurality of reticle cases CS each containing a reticle 1 therein in a hermetically sealed state are mountable in piled relationship on the library RL. An openable-closable door is provided in these cases CS at a position which permits the reticle 1 to be horizontally removed, and the cases CS are mounted on the library RL so that the door faces the space in front of the stepper SR. The structure of such cases CS and the mechanism for mounting them on the library RL are the same as those disclosed in detail, for example, in the aforementioned U.S. Pat. No., 4,422,547 and therefore need not be described herein.

In the present embodiment, however, a case containing therein a reticle with a pellicle can also be mounted on the library RL. The case containing therein the reticle with a pellicle is only thicker by an amount corresponding to the height of the pellicle frame and the basic structure thereof is entirely the same as that disclosed in the aforementioned U.S. patent.

On that side opposed to the library RL with the front space of the stepper SR interposed therebetween, there is disposed a conventional foreign particle checking device (hereinafter referred to as the particle checker) PC for checking foreign particles such as dust on a reticle 1 without a pellicle. This particle checker PC, as disclosed, for example, in U.S. Pat. No. 4,468,120, is provided with a slider 18 for horizontally supporting the reticle 1 thereon and moving it in a horizontal direction (X direction). The particle checker PC is designed such that while the reticle 1 is one-dimensionally scanned by the slider 18, a laser light spot from a laser light source main-scans the surface of the reticle 1 in Y direction orthogonal to X direction and a plurality of photoelectric converters disposed at different positions receive the scattered light from a foreign particle adhering to the reticle 1, whereby on the basis of the photoelectric signals, the presence of adherence of the foreign particle, the position of adherence of the foreign particle, the state of adherence of the foreign particle or the size of the foreign particle is detected. The slider 18 is moved along a guide 19 by a driving device in a driving unit 20.

Also, a pellicle checking device (hereinafter referred to as the pellicle checker) PRC is provided on the lowermost portion of the library RL to check a foreign particle on a reticle with a pellicle, that is, to check relatively large dust adhering onto the pellicle. The basic construction of this pellicle checker PRC is similar to that which is disclosed in Japanese Laid-open Patent Application No. 80546/1982, and will later be described in detail.

It is for the purpose of saving space and making the apparatus compact and for the purpose of not increasing the floor area of the apparatus that the pellicle checker PRC is disposed in a portion of the library RL. Further, the position of the pellicle checker is also a position which enables a reticle with a pellicle removed from one of the cases CS to be quickly conveyed. Originally, a foreign particle is prevented from adhering to the surface of the reticle with a pellicle and therefore, any foreign particle adhering to the pellicle is not resolved up to a considerable size, and the detection accuracy required for the inspection may be much lower than that of the particle checker PC. Instead, it is desired that the time required for the inspection be short.

So, in the present embodiment, means for removing a reticle 1 from one of the cases CS and conveying the reticle 1 to the stepper SR or the particle checker PC is designed to be used also as the one-dimensional scanning means during the inspection by the pellicle checker PRC.

Thus, the means for conveying the reticle 1 will first be described in detail. Two guide struts 9a and 9b are fixed forwardly of the library RL (on the front space side thereof). Sliders 8a and 8b movable in a vertical direction (hereinafter referred to as Z direction) are supported on the guide struts 9a and 9b, respectively, through roller bearings or the like. These two sliders 8a and 8b are fixed to the opposite sides of a horizontal plate 7 and are moved in Z direction by a driving unit 12 including a motor fixed to the lower portion of the guide strut 9a, through a timing belt or the like. A horizontal rotating mechanism unit 6 for turning the reticle is provided on the fore end side of the plate 7. A horizontal guide plate 5 is provided on the mechanism unit 6 and is supported for rotation by approximately 180° in a horizontal plane by the mechanism unit 6. Rotation of the guide plate 5 is effected by a driving unit 11 including a motor fixed to the plate 7. A horizontally moving unit 4 supported for rectilinear movement by a roller bearing or the like is provided on the guide plate 5. A fork-shaped arm 2 for holding only the underside of the marginal portion of a reticle is fixed to the fore end of the horizontally moving unit 4. The horizontally moving unit 4 and the arm 2 are moved together along the guide plate 5 in a rectilinear direction (hereinafter referred to as R direction) by a driving unit 10 including a motor provided on the other end side of the guide plate 5, through a timing belt.

In FIGS. 1 and 2, the arm 2 is shown as being positioned below a reticle 1 in a case CS. A vacuum adsorbing intake hole is formed in the surface of the arm 2 supporting the reticle thereon.

Above the guide plate 5, a positioning mechanism 15 for correcting the positional deviation of the reticle placed on the arm 2 relative to the entire apparatus is suspended through a support arm 14 horizontally extending from above the library RL. This positioning mechanism 15 is of such a structure that it engages the end surfaces of the glass of the reticle from all around it by rollers 15a or the like. Since the positioning mechanism 15 is fixedly disposed high above, the reticle is conveyed to such a position that it is nipped between the rollers 15a, by the movement of the arm 2 in R direction and the movement of the arm 2 in Z direction, whereafter the vacuum adsorption of the arm 2 is released, and then the positioning of the reticle is effected by the rollers 15a.

Also, in the conveying apparatus according to the present embodiment, a bar code reader 24 for reading a bar code formed on the reticle is provided on a plate 7 movable in Z direction. This reader 24 is designed to read the bar code formed around the pattern area of the reticle by a reflection type photosensor, during the movement of the reticle in R direction in which it is drawn out of one of the cases CS. The bar code contains reticle information and is provided with an amount of information corresponding to 10–50 characters representing the distinction of the reticle. The reticle information is read into the stepper SR as the data for the control of the exposure process.

Further, in the present embodiment, ionizers 29 are provided on that side of the plate 7 which is adjacent to the cases CS to prevent a foreign particle from adhering to the surface of the reticle or the surface of the pellicle by charging. The ionizers 29 are disposed so as to put the reticle therebetween above and below the path along which the arm 2 draws a reticle out of one of the cases CS, and inject ionized gas to the upper and lower surfaces of the passing reticle. These ionizers 29 are moved in Z direction with the plate 7 and therefore inject ionized gas to the reticle when the arm 2 carries the reticle into the pellicle checker PRC and when the arm 2 carries the reticle out of the pellicle checker PRC.

Figure 3:
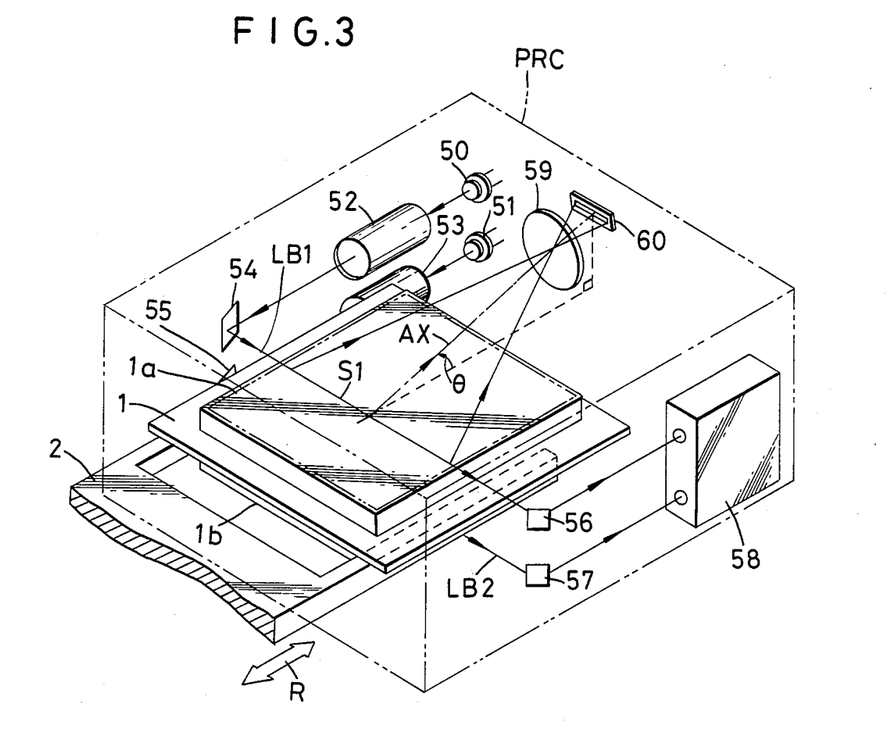
FIG. 3 is a perspective view showing the construction of pellicle checker.

Now, in the present embodiment, the arm 2 for conveying the reticle is designed to effect also the one-dimensional scanning of the reticle in the pellicle checker PRC. So, the specific construction of the pellicle checker PRC will now be described with reference to FIG. 3. FIG. 3 is a perspective view of the pellicle checker PRC as seen from the outlet and inlet side for the reticle. In FIG. 3, a reticle 1 provided with pellicles on the opposite surfaces thereof is placed on the two fork portions of the arm 2. In this case, the pattern surface (the surface formed with chromium) of the reticle 1 is the underside, and with the glass surface of the back (upper surface) of the pattern surface, it has secured thereto pellicle frames 1a and 1b. The spacing between the two fork portions of the arm 2 is determined to such a degree that the frame 1b does not strike thereagainst but is put therebetween. Also, the heights of the frames 1a and 1b are accurately determined in advance, and the spacing between the pellicles on the opposite surfaces is determined so as to be identical in any reticle.

In the pellicle checker PRC, there is provided a laser light supplying system comprising two semiconductor laser light sources 50, 51, lens systems 52, 53 for forming the laser light from the laser light sources into substantially parallel condensed laser light beams LB1, LB2, and mirrors 54, 55 for applying the parallel laser light beams LB1, LB2 from the lens systems 52, 53 substantially horizontally to the pellicle on the upper surface and the pellicle on the lower surface, respectively. The application orbit S1 on the pellicles by the laser light beams LB1, LB2 is determined so as to extend slenderly in a direction orthogonal to the movement of the arm 2 in R direction. Further, the laser light beams LB1 and LB2 applied to the pellicles are reflected by mirrors 56 and 57, respectively, whereafter they enter a light trap 58 so as not to be stray light in the pellicle checker PRC and are absorbed in this light trap. The vertical spacing between the laser light beams LB1 and LB2 is determined so as to be equal to the spacing between the pellicles on the upper and lower surfaces. Accordingly, if the arm 2 is determined at a predetermined position in Z direction and is advanced in R direction, the pellicles on the upper and lower surfaces will be scanned at the same time by the laser light beams LB1 and LB2.

If a foreign particle is present on the application orbit S1 of the laser light, scattered light of weak directionality will be produced from the foreign particle. So, in the present embodiment, there is provided a photoelectric detecting system comprising a condensing lens 59 for reducing and imaging the application orbit S1, and a one-dimensional photoarray 60 for receiving the image of the application orbit S1.

The optic axis AX of the condensing lens 59 marks substantially the center of the application orbit S1 and the angle $\theta$ formed between the optic axis AX and the pellicle surface is determined to an acute angle less than 90°, preferably to the order of 10°–20°.

The one-dimesional photoarray 60 is, for example, a self-scanning type CCD array, and divides the application orbit S1 into a plurality of areas in the lengthwise direction and is provided with a plurality of light-receiving elements (picture elements) for individually receiving the scattered light from the respective areas. By reading each picture element of the one-dimensional photoarray 60 in synchronism with the unit movement (e.g., 1 mm) of the arm 2 in R direction, it is possible to detect the position and size of the foreign particle on the application orbit S1. By providing in the driving unit 10 means (such as an encoder) for reading the amount of movement of the arm 2 in R direction, it is possible to detect the two-dimensional position of the foreign particle on the pellicle.

In the present embodiment, an entirely similar photoelectric detecting system is also provided for the foreign particle on the pellicle on the lower surface, and the inspections of the pellicles on the upper and lower surfaces can be executed at the same time during one scan of the arm 2, and more specifically, during the scan in which the reticle 1 is drawn out after it has once been brought into the innermost part and therefore, the inspection time is greatly shortened. Moreover, in the case of the inspection of the pellicles, accuracy is not so required and therefore, an inspection much higher in speed than the inspection of the particle checker PC in which a light spot is scanned by a vibratory mirror, a polygon mirror or the like.

Exemplarily showing the specific numerical value of the inspection time, if the read-out cycle of the one-dimensional photoarray 60 is 1/60 sec. and the length of the pellicle surface in R direction is 10 cm and the area on the pellicle surface in which a picture element of the one-dimensional photoarray 60 receives light is 100 $\mu m \times 100$ $\mu m$, the time required to inspect the whole of the pellicle surface is maximum 16.6 sec. (1/60 × 100/0.1). Of course, if the area in which a picture element receives light is doubled, a high-speed inspection requiring a time of 10 sec. or less will be possible. However, the factors which determine the inspection time include the velocity of movement and the stability of rectilinear movement of the arm 2. Particularly, deviation or deflection of the arm 2 in Z direction directly leads to an error of the result of inspection.

Figure 4:
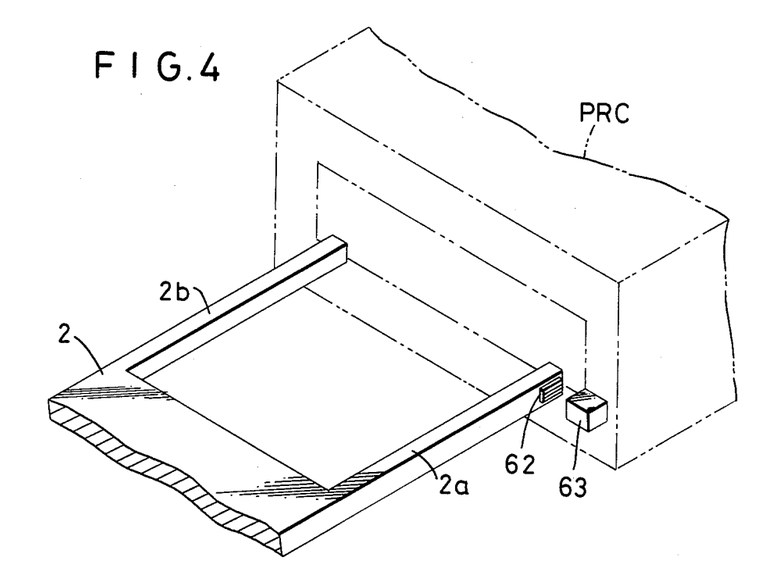
FIG. 4 is a perspective view showing the disposition of a photosensor for detecting the position of an arm.

So, in the present embodiment, a photosensor for detecting whether the position of the height of the arm 2 is proper is provided near the outlet and inlet for the pellicle checker PRC.

FIG. 4 shows the relation between the disposition of the photosensor and the arm 2. In FIG. 4, the reticle place on the arm 2 is not shown. A small piece of glass 62 is attached to the side of the fore end of the fork portion 2a of the two fork portions 2a and 2b of the arm 2. A reflective pattern of chromium or the like linearly extending in R direction is formed on the small piece of glass 62. A reflection type photosensor 63 is provided so as to most intensely receive the reflected light from the reflective pattern of the small piece of glass 62 when the arm 2 is disposed at a prescribed position in Z direction. Accordingly, if the arm 2 is scanned in R direction after the position of the arm 2 in Z direction has been determined by the driving unit 12 so that the photoelectric output of the photosensor 63 is greatest, the two laser light beams LB1 and LB2 will be accurately applied to the surfaces of the pellicles, respectively, on the upper and lower surfaces.

Also, it is conceivable that the arm 2 is inclined in a direction orthogonal to R direction relative to the horizontal plane. It is therefore desirable to provide a similar small piece of glass also on the fore end of the other fork 2b of the arm 2 and detect it by a photosensor, thereby detecting the inclination of the arm 2 from the outputs of the two photosensors. Further, it may also happen that the arm 2 is inclined in R direction relative to the horizontal plane by the weight or the like of the reticle. In that case small pieces of glass 62 may be attached, for example, to a plurality of portions of the side of the fork portion 2a (or 2b) along R direction, and the arm 2 may be moved in R direction with the position of the arm 2 in Z direction remaining fixed, whereby how the output of the photosensor 63 varies each time the small pieces of glass 62 pass may be detected. Alternatively, the inclination of the arm 2 can be likewise detected by effecting the positioning of the arm 2 in R direction so that the small pieces of glass 62 are opposed to the photosensor, thereafter the minute vertical movement of the arm 2 in Z direction and the memorization of the Z position at which the photoelectric output has become maximum, with respect to each of the small pieces of glass 62 provided on the side of the fork portion 2a (or 2b).

Further, if a plurality of such photosensors 63 are disposed in the predetermined path of the arm 2 in the pellicle checker PRC, the posture of the arm 2, i.e., the horizontality of the pellicle surface, can be confirmed every moment even during the inspection of the pellicle and thus, the reliability of the inspection will be more improved.

Now, the arm 2 rectilinearly moves in R direction and also turns while adsorbing the reticle. Therefore, unless some contrivance is provided for the drawing-about of a tube for directing the vacuum system to the fork portions 2a and 2b of the arm, the tube will be caught by another mechanism portion due to the movement of the arm and thereby cause trouble in the mechanical system. In the present embodiment, a mechanism for taking up the tube is provided on a portion of the guide plate 5 so that the tube may not be slackened or entangled by the movement of the arm 2.

Figure 5:
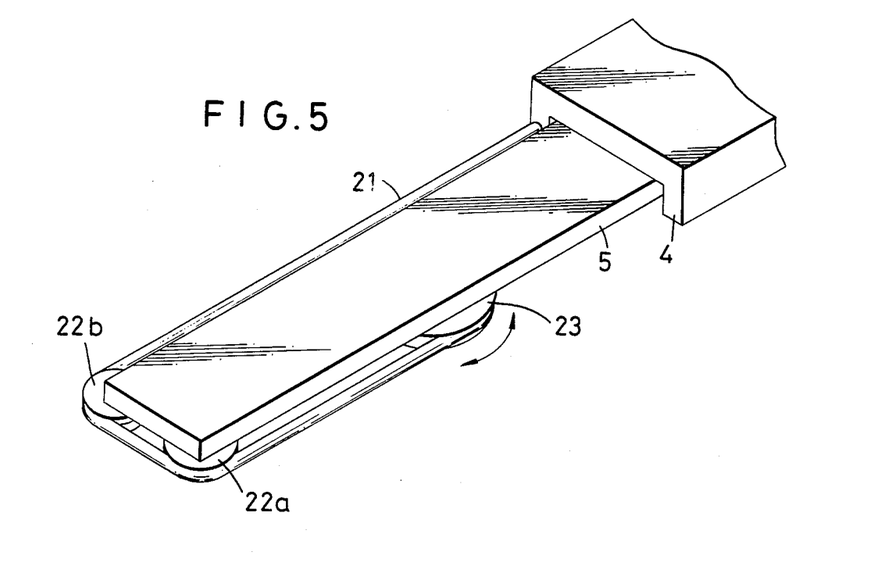
FIG. 5 is a perspective view showing the structure of the tube take-up mechanism of a vacuu adsorbing system.
Figure 6:
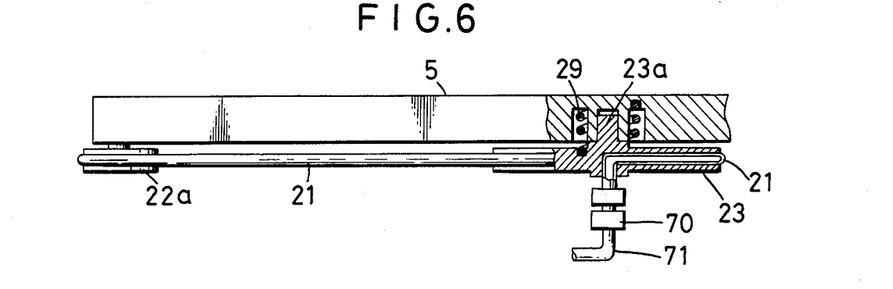
FIG. 6 is a partial cross-sectional view of the take-up mechanism.

FIG. 5 schematically shows the construction of the take-up mechanism, and FIG. 6 shows a partial cross-section thereof. The horizontal moving portion 4 for moving the arm 2 in R direction is provided on the guide plate 5, and fixed piping for vacuum drawing is provided up to the fork portions 2a and 2b of the arm 2 through the horizontal moving portion 4. A flexible tube 21 extends rearwardly from the horizontal moving portion 4 along the guide plate 5, is turned back in U-shape through two pulleys 22b and 22a rotatably supported on the lower portion of the guide plate 5, and is mounted so as to be taken up by a take-up pulley 23.

This pulley 23 is rotatably provided below the guide plate 5 coaxially with the center of rotation of the guide plate 5 by the horizontal rotating mechanism portion 6 and is moreover disposed so as not to mechanically interfere with the movement of the horizontal moving portion 4 in R direction. The pulley 23 is normally biased in the direction of rotation for taking up the tube 21.

The pulley 23, as shown in FIG. 6, is journalled to the guide plate 5 through a shaft 23a, and a coil spring 29 is provided around and coaxially with the shaft 23a. The coil spring 29 has one end thereof fixed to the guide plate 5 and the other end thereof fixed to the pulley 23, and normally biases the pulley 23 for rotation in one direction. The end of the tube 21 taken up by the pulley 23 is drawn out in the pulley 23 along and substantially coaxially with the center of rotation, and is connected to a tube 71 through a rotatable joint 70. The tube 71 in turn is connected to a vacuum exhaust system, not shown.

In the construction as described above, when the arm 2 moves in R direction, the pulley 23 rotates relative to the guide plate 5 and effects the take-up or feed-out of the tube 21. Also, when the guide plate 5 is rotated in θ direction without the arm 2 being moved in R direction, the pulley 23 rotates with the rotation of the guide plate 5. Thus, by the draw-out positions of the tubes 21 and 71 being made substantially coincident with the center of rotation of the guide plate 5, twist or entanglement of the drawn-out tube 71 is prevented, whereby trouble in the mechanical system is eliminated.

Figure 7:
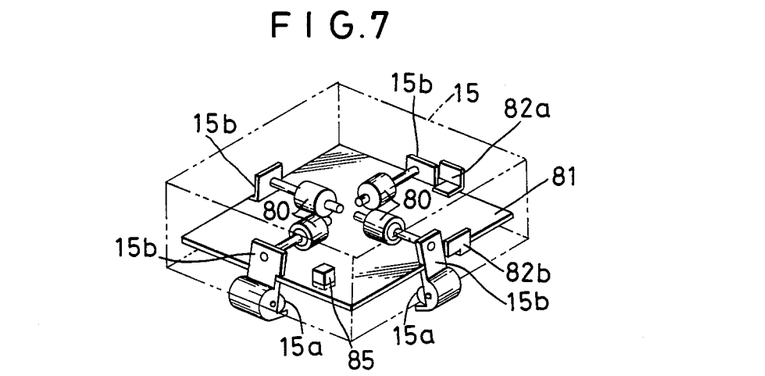
FIG. 7 is a perspective view of a reticle positioning mechanism.
Figure 8:
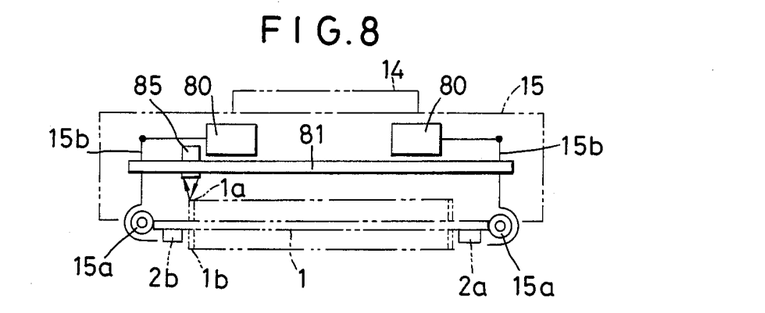
FIG. 8 is a schematic view as seen from a side of FIG. 7.

Now, the reticle conveyed by the arm 2 is positioned relative to the apparatus as required. FIG. 7 is a perspective view showing the construction of a positioning mechanism 15, and FIG. 8 is a schematic side view thereof. Rocking portions 15b rockable by respective air cylinders 80 and supporting rollers 15a on the lower portion thereof are provided on the four sides of a base plate of a size and shape similar to those of the reticle. Positioning of the reticle is accomplished by the glass end surfaces of the reticle being grasped by these rollers 15a. For the purpose of this positioning, there are provided stops 82a and 82b for controlling the positions of the rocking portions 15a. A reflection type photosensor 85 for detecting whether the reticle is a reticle with a pellicle is provided on the underside of the base plate 81. This photosensor 85, as shown in FIG. 8, is disposed so as to apply light to the upper end surface of the pellicle frame 1a on the upper surface of the reticle and receive the reflected light therefrom when the rollers 15a hold the reticle therebetween. Also, the spacing in the direction of height from the underside of the base plate 81 to the roller 15a is determined so as to be greater than the height dimension of the frame of the conveyed reticle with a pellicle.

In such a construction, when positioning the reticle, the arm 2 is first positioned below the positioning mechanism 15, whereafter the arm 2 is moved up in Z direction. At this time, the rollers 15a are open and, at a point of time whereat the reticle has reached the same level as the rollers 15a, the upward movement of the arm 2 is stopped. Then, the vacuum adsorption by the tube 21 is released to permit the reticle to move freely in the horizontal plane on the fork portions 2a and 2b of the arm 2. Subsequently, the cylinders 80 are operated to urge the rollers 15a against the end surfaces of the reticle, thereby accomplishing the positioning of the reticle. At this time, the reticle slightly slides on the fork portions 2a and 2b and therefore, synthetic resin such as Teflon or Delrin may preferably be provided around the portion which is in contact with the reticle, for example, around the vacuum adsorption hole. With the rollers 15a holding the reticle therebetween, the fork portions 2a and 2b again start the vacuum adsorption of the reticle and finally, the rollers 15a are opened, whereupon a series of positioning operations are completed.

It is desirable that these positioning operations be effected immediately after a reticle has been removed from one of the cases CS or immediately before the reticle is returned to one of the cases CS. Also, to keep the accuracy of delivery of the reticle between the apparatuses, the positioning of the reticle may be effected as required.

The conveyance sequence by the apparatus according to the present embodiment will now be described. When a reticle with a pellicle is to be conveyed to the stepper SR, the arm 2 is positioned in front of the door of a desired one of the cases CS. A door opening-closing mechanism disclosed in the aforementioned U.S. Pat. No. 4,422,547 is provided on the plate 7 movable in Z direction, and only the door of the case CS relative to which the arm 2 has been positioned is opened. Thereafter, the arm 2 comes into under the reticle 1 in the case CS, and the reticle 1 is placed onto the arm 2 with the aid of the vacuum adsorption by the fork portions 2a and 2b, whereafter the reticle 1 is horizontally taken out of the case CS. The arm 2 is then moved in R direction to just beneath the positioning mechanism 15 by the driving unit 10, whereafter it is moved up in Z direction by the driving unit 12, and the reticle 1 is positioned as shown in FIG. 8.

Subsequently, the arm 2 is intactly lowered to the position of the lowermost pellicle checker PRC and is further moved in R direction, and the reticle 1 is horizontally scanned in the pellicle checker PRC to inspect the foreign particle on the pellicle, as shown in FIG. 3. If, in this inspection, foreign particles enough to be resolved and transferred by the stepper SR are detected, the arm 2 is moved so as to return the reticle 1 into the original case CS. When a foreign particle is absent or it is judged that even if a foreign particle is present, it will not affect the transfer, the arm 2 is drawn out of the pellicle checker PRC, whereafter it is turned by 90° in counter-clockwise direction from the position of FIG. 1 by the operation of the horizontal rotating mechanism unit 6 and is moved up in Z direction and stopped at a height position for the delivery to the stage 30 of the stepper SR. Then, the arm 2 is moved in R direction to place the reticle 1 onto the stage 30. A similar effect may be obtained by adopting such a sequence that after the arm 2 has been drawn out of the pellicle checker PRC, the arm 2 is moved up in Z direction and then is turned by 90° in counter-clockwise direction.

Now, in the case of a reticle without a pellicle, it is conveyed to the particle checker PC instead of to the pellicle checker PRC, whereby it is inspected as to the presence of foreign particles, whereafter it is fed into the stepper SR. In that case, after the reticle has been positioned, the arm 2 is lowered to the height position of the slider 18 of the particle checker PC, whereafter the guide plate 5 is rotated by 180° in counter-clockwise direction from the position of FIG. 1. At this time, the slider 18 is drawn most out of the particle checker PC, and the arm 2 turns slightly above the slider 18 so as not to interfere with the slider 18, thereby positioning the reticle 1 just above the slider 18. This sequence may be converse, that is, the slider 18 may be drawn out below the arm 2 after the arm has turned by 180°.

When the vacuum adsorption of the fork portions 2a and 2b is then released and the arm 2 is lowered, the fork portions 2a and 2b of the arm 2 slide through the U-shaped interior of the slider 18 and the marginal portion of the reticle 1 is placed onto the slider 18. Subsequently, the slider 18 enters the particle checker PC and predetermined inspection of foreign particle is effected. When a foregin particle is absent, the arm 2 is moved up in a position wherein the slider 18 has been most drawn out, and receives the reticle 1 and turns the reticle 1 by 90° in clockwise direction as viewed in FIG. 1, whereafter the reticle 1 is fed into the stepper SR. Of course, when any foreign particle has been found out, the arm 2 turns by 180° in clockwise direction and that reticle 1 is returned into the original case CS.

The bar code reader 24 shown in FIG. 1 may b provided within the stepper SR and designed to judge whether the reticle fed in is right. However, if the reader 24 is provided as shown in FIG. 1, confirmation of the reticle and re-containment of a wrong reticle into one of the cases CS can be accomplished simply by rectilinear movement of the arm 2 and thus, high-speed operation is achieved. The reader 24 is designed to project onto the back surface (pattern surface) of the reticle a slit-shaped optical image extending in a direction orthogonal to the direction in which reticles are drawn out of the cases CS, and receive the reflected light from the bar code formed of reflective chromium. Also, the bar code on the reticle is provided around the pattern area at such a position whereat the light is not intercepted by the fork portions 2a and 2b.

While the present embodiment has been described above, the pellicle checker PRC can also effect foreign particle inspection with respect to a reticle without a pellicle to a certain degree. As shown in FIG. 3, the laser light beams LB1 and LB2 for inspection are applied parallel to the upper and lower surfaces of the reticle and therefore, for example, the glass surface of the reticle on which the pattern is not formed can be inspected in the same manner as the foreign particle inspection of the pellicle surface. In this case, by the use of the photosensor 63 (see FIG. 4) for detecting the height of the arm 2, the arm 2 may be adjusted in Z direction so that the glass surface of the reticle becomes coincident with the height of the laser light beam LB1. Also, the spacing between the laser light beams LB1 and LB2 may be secured sufficiently so that the pellicle surface on the upper surface of the reticle may be scanned by the laser light beam LB1 when the reticle comes in and that the pellicle surface on the lower surface of the reticle may be scanned by the laser light beam LB2 with the reticle being slightly lowered when the reticle is drawn out.

Further, the particle checker PC in the present embodiment is provided with the slider 18 exclusively for one-dimensional scanning of the reticle. This is because in such a light spot scanning type foreign particle inspecting apparatus of high detection resolving power, it is necessary to make the accuracy of one-dimensional movement of the reticle considerably high. However, if provision is made of a roller and a guide member for supporting the fork portions 2a and 2b of the arm 2 which have come into the particle checker PC so that the stability of the rectilinear movement thereof in R direction and Z direction is improved, the slider 18 will become unnecessary and the period of delivery of the reticle will be further decreased.

Also, the library RL may be so disposed that the cases CS can be mounted from the front side of the entire apparatus. That is, the library RL is provided at a position in which it has been rotated by 90° in clockwise direction about the axis of rotation of the guide plate 5 from the position of FIG. 1. In this case, the door of the cases CS becomes opposed to the stepper SR.

Further, while the present embodiment has been described as a conveying apparatus suitable for an apparatus such as a stepper for applying treatment to a workpiece such as a wafer by the use of a reticle, the present embodiment can obtain a similar effect also as a conveying apparatus comprising a combination of an apparatus for applying some treatment to a reticle or a mask itself, such as a reticle cleaning apparatus or a pattern modifying apparatus, and a foreign particle inspecting apparatus. Also, in the pellicle checker PRC, the pellicle surface and the laser light beams, LB1, LB2 are made coincident with each other by detecting the height position or the inclination of the arm 2 by means of the photosensor 63, but if provision is made of a sensor for directly detecting the height position of the pellicle surface, a similar inspection will be possible whatever the height of the pellicle frame may be. Further, the photosensor 85 provided on the positioning mechanism 15 is not limited to the reflection type, but may also be of the transmission type. In the latter case, the photosensor need be such that light is projected onto a side surface of the pellicle frame and the light is received by the opposite side surface of the pellicle frame. Whether the reticle is a reticle with a pellicle is judged by whether the light is intercepted by the pellicle frame.

We claim:

1. An arrangement in an apparatus for handling a substrate such as a photomask or a reticle used in a process of manufacturing a semiconductor device, comprising:
    a container unit for containing therein said substrate in a substantially horizontal posture;
    an inspection unit having means for inspecting a surface of said substrate, said inspecting means including radiation means for supplying a directional beam to said surface, and means for detecting scattering of said directional beam from the surface of said substrate;
    a holding member for holding said substrate substantially horizontally;
    a support member having a guide member for supporting said holding member movably in a horizontal direction;
    first drive means for moving said support member between a first position wherein said guide member is opposed to said container unit and a second position wherein said guide member is opposed to said inspection unit;
    second drive means for moving said holding member relative to said guide member;
    third drive means operable to fix said substrate to said holding member and to separate said substrate from said holding member; and
    operation means for controlling said first, second and third drive means so that, when said support member is moved in said first position, said substrate is fixed to said holding member and said holding member is moved by said second drive means to remove said substrate from said container unit, and when said support member is in said second position, said holding member is moved by said second drive means together with said substrate to cause a relative displacement between said substrate and said directional beam for inspecting said substrate by said inspecting means.

2. An arrangement according to claim 1, wherein said holding member moves linearly along one direction.

3. An arrangement according to claim 1, wherein said directional beam is emitted along an optic axis substantially parallel with a horizontal plane, and wherein when said support member is in said second position, said substrate is moved in a direction intersecting said optic axis along said horizontal plane by said second drive means so that said surface of said substrate substantially coincides with said horizontal plane.

4. An arrangement according to claim 3, wherein said detecting means includes one-dimensional image sensing means and condensing means provided between said optic axis and said image sensing means for imaging the scattering of said directional beam emanating from said surface of said substrate on said image sensing means.

5. An arrangement according to Claim 1, wherein said inspection unit includes a housing provided with an opening through which pass said holding member and said substrate moved in the horizontal direction by said second drive means, and a detector fixedly disposed relative to said housing near said opening and detecting the position of the surface of said substrate supported by said holding member.

6. An arrangement according to Claim 1, further comprising ion generating means stationarily disposed in opposed relationship with the surface of said substrate supported by said holding member inserted in said container unit.

7. An arrangement according to claim 1, wherein said container unit and said inspection unit are series-arranged in a substantially vertical direction, and said first drive means includes a vertically moving unit for moving said support member in a vertical direction, and a horizontally moving unit for moving said support member in a horizontal direction and causes said guide member opposed to said inspection unit by said vertically moving unit to be moved in a horizontal direction by operating said horizontally moving unit.

8. An arrangement in an apparatus for handling substrates such as photomasks or reticles used in a process of manufacturing semiconductor devices, said substrates including a first kind of substate having at least one surface thereof protected by a transparent pellicle and a second kind of substrate not protected by said pellicle, aid arrangement comprising:
    a container unit for containing therein said first kind of substate and said second kind of substrate in substantially horizontal postures;
    a first inspection unit having means for inspecting a foreign particle on a surface of said pellicle of said first kind of substrate, said inspecting means including radiation means for supplying directional beam to said surface, and means for detecting scattering of said directional beam from said surface;
    a second inspection unit for inspecting a surface of said second kind of substrate;
    a holding member for supporting either one of said first kind of substrate and said second kind of substrate substantially horizontally;
    a support member having a guide member for supporting said holding member movably in a horizontal direction;
    first drive means for moving said support member between a first position wherein said guide member is opposed to said container unit, a second position wherein said guide member is opposed to said first inspection unit and a third position wherein said guide member is opposed to said second inspection unit;
    second drive means for moving said holding member relative to said guide member;
    third drive means operable to fix a substraste to said holding member and to separate that substrate from said holding member; and
    operation means for controlling said first, second and third drive means so that when said support member is in said first position, a substrate supported thereby is fixed to said holding member and said holding member is moved by said second drive means to remove the supported substrate from said container unit, so that when said support member is in said second position, said holding member is moved by said second drive means together with the supported substrate to cause a relative displacement between the supported substrate and said directional beam for inspecting said substrate by said inspecting means of said first inspection unit, and so that when said support member is in said third position, said holding member is moved by said second drive means to transfer the supported substrate into said second inspection unit.

9. An arrangement according to claim 8, further comprising means for discriminating whether a substrate supported by said holding member is said first kind of substrate or said second kind of substrate, and wherein said first drive means moves said support member into said second position when said holding member supports said first kind of substrate and moves said support member into said third position when said holding member supports said second kind of substrate.

10. An arrangement in an apparatus for handling a substrate such s a photomask or a reticle used in a process of manufacturing a semiconductor device, comprising:

a container unit for containing therein said substrate;
an inspection unit having means for inspecting a surface of said substrate, said inspecting means including radiation means for supplying a directional beam to said surface, and means for detecting scattering of said directional beam from said surface of said substrate;
a holding member for holding said substrate;
a support member for movably supporting said holding member thereon;
first drive means for moving said support member between a first position wherein said holding member is opposed to said container unit and a second position wherein said holding member is inserted into said inspection unit; and
second drive means for moving said holding member into said container unit to hold said substrate and to remove said substrate from said container unit when said support member is moved in said first position, and for moving said holding member in said inspection unit to cause a relative displacement between said substrate held by said holding member and said directional beam for inspecting said substrate by said inspecting means when said support member is moved in said second position.

11. An arrangement in an apparatus for handling a substrate such as a photomask or a reticle used in a process of manufacturing a semiconductor device, comprising:

a container unit for containing therein said substrate;
an inspection unit having means for inspecting a surface of said substrate, said inspecting means including radiation means for supplying a directional beam to said surface, and means for detecting scattering of said directional beam from said surface of said substrate;
a holding member for holding said substrate; and
operation means for moving said holding member into said container unit to hold said substrate and to remove said substrate form said container unit, for transporting said holding member from said container unit into said inspection unit, and for moving said holding member in said inspection unit to cause a relative displacement between said substrate held by said holding member and said directional beam for inspecting said substrate by said inspecting means.

* * * * *